(12) United States Patent
Arzt et al.

(10) Patent No.: US 9,623,169 B2
(45) Date of Patent: Apr. 18, 2017

(54) METHOD AND SYSTEM FOR FILLING AND VENTING A DEVICE FOR EXTRACORPOREAL BLOOD TREATMENT, WITH STEPPED FLOODING OF A FILTER

(75) Inventors: Joachim Arzt, Reichenbach (DE); Gerhard Brieske, Ampfing (DE); Florian Sagebiel, Lohbarbek (DE)

(73) Assignee: ZOLL LifeBridge GmbH, Ampfing (DE)

( * ) Notice: Subject to any disclaimer, the term of this patent is extended or adjusted under 35 U.S.C. 154(b) by 0 days.

(21) Appl. No.: 13/989,374

(22) PCT Filed: Dec. 7, 2011
(Under 37 CFR 1.47)

(86) PCT No.: PCT/EP2011/072143
§ 371 (c)(1),
(2), (4) Date: Dec. 10, 2013

(87) PCT Pub. No.: WO2012/076632
PCT Pub. Date: Jun. 14, 2012

(65) Prior Publication Data
US 2014/0326678 A1     Nov. 6, 2014

Related U.S. Application Data

(63) Continuation of application No. 12/962,618, filed on Dec. 7, 2010, now Pat. No. 8,834,399, and a
(Continued)

(30) Foreign Application Priority Data

| Dec. 7, 2010 | (EP) | 10194069 |
| Dec. 7, 2010 | (EP) | 10194070 |
| Dec. 7, 2010 | (EP) | 10194071 |

(51) Int. Cl.
*A61M 1/36* (2006.01)
*A61M 1/34* (2006.01)
(Continued)

(52) U.S. Cl.
CPC ......... *A61M 1/3666* (2013.01); *A01N 1/0247* (2013.01); *A61M 1/1698* (2013.01);
(Continued)

(58) Field of Classification Search
CPC .............. A61M 1/1698; A61M 1/3621; A61M 1/3624; A61M 1/3626; A61M 1/3627;
(Continued)

(56) References Cited

U.S. PATENT DOCUMENTS

| 3,567,028 A | 3/1971 | Nose |
| 3,744,762 A | 7/1973 | Schlicht |

(Continued)

FOREIGN PATENT DOCUMENTS

| CN | 1217669 A | 5/1999 |
| CN | 1909938 A | 2/2007 |

(Continued)

OTHER PUBLICATIONS

European Search Report dated Aug. 22, 2014 in related European Application No. 13196715.0.
(Continued)

*Primary Examiner* — Adam Marcetich
(74) *Attorney, Agent, or Firm* — Robert D. Buyan; Stout, Uxa & Buyan, LLP

(57) ABSTRACT

A method for filling and venting a device for extracorporeal blood treatment is disclosed, such as a patient module in a heart-lung machine, without attached patient. A filling liquid from a filling liquid container located higher than the device flows by gravity via a venous side of the system into a reservoir and flows onwards into a blood pump located at the
(Continued)

lower end of the reservoir, wherein a first controllable valve (HC1) for a venting line of a filter is opened and, after the response of an upper filling level sensor in the reservoir, is closed. An upper level of the filter is positioned higher than the upper filling level sensor, and a start-stop motion of the blood pump is performed, as a result of which a stepped flooding of the filter is made providing for an advantageous de-airing of the device.

14 Claims, 7 Drawing Sheets

Related U.S. Application Data continuation of application No. 12/962,622, filed on Dec. 7, 2010, now Pat. No. 8,882,693, and a continuation of application No. 12/962,626, filed on Dec. 7, 2010, now Pat. No. 8,721,579.

(60) Provisional application No. 61/420,758, filed on Dec. 7, 2010, provisional application No. 61/420,760, filed on Dec. 7, 2010, provisional application No. 61/420,763, filed on Dec. 7, 2010.

(51) Int. Cl.
*A61M 1/16* (2006.01)
*A01N 1/02* (2006.01)
*A61M 1/10* (2006.01)
*F16K 31/00* (2006.01)
*F16K 35/00* (2006.01)

(52) U.S. Cl.
CPC ........ *A61M 1/3621* (2013.01); *A61M 1/3626* (2013.01); *A61M 1/3627* (2013.01); *A61M 1/3629* (2014.02); *A61M 1/3632* (2014.02); *A61M 1/3643* (2013.01); *A61M 1/3644* (2014.02); *A61M 1/3659* (2014.02); *A01N 1/02* (2013.01); *A01N 1/0236* (2013.01); *A01N 1/0242* (2013.01); *A61M 1/101* (2013.01); *A61M 1/3624* (2013.01); *A61M 1/3633* (2013.01); *A61M 2205/33* (2013.01); *A61M 2205/3389* (2013.01); *A61M 2205/7536* (2013.01); *F16K 31/00* (2013.01); *F16K 35/00* (2013.01)

(58) Field of Classification Search
CPC .............. A61M 1/3629; A61M 1/3632; A61M 1/3643; A61M 1/3644; A61M 1/3666; A61M 2205/3389; A61M 2205/3379; A61M 2205/3382; A61M 2205/3386; A61M 1/3649; A61M 2205/52
See application file for complete search history.

(56) References Cited

U.S. PATENT DOCUMENTS

| | | | |
|---|---|---|---|
| 4,466,804 A | 8/1984 | Hino | |
| 4,562,984 A | 1/1986 | Sherlock et al. | |
| 4,612,170 A | 9/1986 | Luther et al. | |
| 4,620,965 A | 11/1986 | Fukusawa et al. | |
| 4,781,525 A * | 11/1988 | Hubbard et al. | 415/30 |
| 4,876,066 A | 10/1989 | Bringham et al. | |
| 4,925,152 A | 5/1990 | Huber | |
| 5,084,244 A | 1/1992 | Muramoto | |
| RE33,932 E | 5/1992 | Fukasawa et al. | |
| 5,188,604 A | 2/1993 | Orth | |
| 5,227,049 A * | 7/1993 | Chevallet et al. | 210/97 |
| 5,232,437 A | 8/1993 | Lysaght et al. | |
| 5,350,357 A | 9/1994 | Kamen et al. | |
| 5,391,142 A | 2/1995 | Sites et al. | |
| 5,437,634 A * | 8/1995 | Amano | 604/65 |
| 5,529,685 A | 6/1996 | Irie et al. | |
| 5,676,526 A * | 10/1997 | Kuwana et al. | 417/53 |
| 5,798,454 A * | 8/1998 | Nakazeki et al. | 73/54.28 |
| 5,820,579 A | 10/1998 | Plotkin | |
| 5,823,986 A | 10/1998 | Peterson | |
| 5,950,670 A | 9/1999 | Flaim | |
| 6,010,633 A | 1/2000 | Zuk et al. | |
| 6,039,078 A | 3/2000 | Tamari | |
| 6,071,257 A | 6/2000 | Stojanovic | |
| 6,071,258 A | 6/2000 | Dalke et al. | |
| 6,302,860 B1 | 10/2001 | Gremel et al. | |
| 6,386,505 B2 | 5/2002 | Schob | |
| 6,579,257 B1 | 6/2003 | Elgas et al. | |
| 6,695,803 B1 | 2/2004 | Robinson et al. | |
| 6,748,815 B2 | 6/2004 | Povey et al. | |
| 7,367,540 B2 | 5/2008 | Brieske | |
| 7,597,546 B2 | 10/2009 | Brieske | |
| 7,762,976 B2 | 7/2010 | Schreyer et al. | |
| 2002/0012988 A1 | 1/2002 | Brasile | |
| 2002/0031442 A1 | 3/2002 | Knott | |
| 2002/0085952 A1* | 7/2002 | Ellingboe et al. | 422/45 |
| 2002/0138034 A1 | 9/2002 | Derek et al. | |
| 2002/0176798 A1 | 11/2002 | Linker et al. | |
| 2003/0111403 A1* | 6/2003 | Zia | B01D 27/07 210/436 |
| 2003/0163077 A1* | 8/2003 | Kim | A61M 1/16 604/5.01 |
| 2003/0209475 A1* | 11/2003 | Connell | A61M 1/16 210/143 |
| 2004/0195178 A1* | 10/2004 | Carpenter et al. | 210/645 |
| 2005/0004480 A1 | 1/2005 | Kirchhof | |
| 2005/0063860 A1 | 3/2005 | Carpenter et al. | |
| 2005/0085762 A1 | 4/2005 | Vijay et al. | |
| 2005/0090774 A1 | 4/2005 | Tonelli et al. | |
| 2006/0122551 A1* | 6/2006 | Brieske | 604/4.01 |
| 2007/0146342 A1 | 6/2007 | Medler et al. | |
| 2007/0239381 A1* | 10/2007 | Ginggen | A61M 5/14276 702/100 |
| 2008/0171960 A1* | 7/2008 | Brieske et al. | 604/4.01 |
| 2008/0221498 A1* | 9/2008 | Ogihara et al. | 604/6.11 |
| 2008/0230473 A1* | 9/2008 | Herbst | 210/634 |
| 2008/0262405 A1* | 10/2008 | Ogihara et al. | 604/6.15 |
| 2009/0004053 A1 | 1/2009 | Kenley | |
| 2009/0076433 A1* | 3/2009 | Folden et al. | 604/4.01 |
| 2009/0230036 A1 | 9/2009 | Apel et al. | |
| 2009/0298043 A1 | 12/2009 | Mangino | |
| 2009/0312686 A1* | 12/2009 | Sakamoto | A61M 1/3643 604/6.11 |
| 2010/0234928 A1 | 9/2010 | Rakhorst et al. | |
| 2011/0168291 A1* | 7/2011 | Beden | A61M 1/3643 141/1 |
| 2011/0213289 A1* | 9/2011 | Toyoda | A61M 1/3643 604/6.09 |

FOREIGN PATENT DOCUMENTS

| | | |
|---|---|---|
| CN | 101193669 A | 6/2008 |
| CN | 101193670 A | 6/2008 |
| CN | 101829371 A | 9/2010 |
| DE | 1284044 B | 11/1968 |
| DE | 2138513 | 3/1972 |
| DE | 3834952 A1 | 4/1989 |
| DE | 19534502 A1 | 3/1997 |
| DE | 29719899 U1 | 1/1998 |
| DE | 19702098 A1 | 7/1998 |
| DE | 19905937 C1 | 7/2000 |
| EP | 0171749 A1 | 2/1986 |
| EP | 0223864 A1 | 6/1987 |
| EP | 1457218 A1 | 9/2004 |
| EP | 1661592 A1 | 5/2006 |
| EP | 1698371 A1 | 9/2006 |
| EP | 1705375 A1 | 9/2006 |
| EP | 1982739 A1 | 10/2008 |
| FR | 2368284 A1 | 5/1978 |
| JP | 2002527212 T | 8/2002 |
| JP | 2002536126 T | 10/2002 |

(56) References Cited

FOREIGN PATENT DOCUMENTS

| | | | |
|---|---|---|---|
| JP | 2003180824 A | 7/2003 |
| WO | WO9511709 A2 | 5/1995 |
| WO | WO02/26286 A2 | 4/2002 |
| WO | WO0226288 A2 | 4/2002 |
| WO | WO2004098678 A1 | 11/2004 |
| WO | WO2005/065743 A1 | 7/2005 |
| WO | 2006/120415 A1 | 11/2006 |

OTHER PUBLICATIONS

PCT International Search Report dated Feb. 29, 2012 in related PCT Application No. PCT/EP2011/072143.
United States Patent & Trademark Office Notice of Allowance mailed Oct. 4, 2010 in U.S. Appl. No. 11/284,515, 8 pages.
United States Patent and Trademark Office, Office Action mailed Apr. 21, 2010 in U.S. Appl. No. 11/284,515, 11 pages.
Japanese Patent Office, Examiner's Report mailed Dec. 22, 2009 in Japanese Patent Application No. JP2005-335622, 4 pages.
United States Patent and Trademark Office, Final Office Action mailed Dec. 8, 2009 in U.S. Appl. No. 111284,515, 10 pages.
United States Patent and Trademark Office, Office Action mailed May 27, 2009 in U.S. Appl. No. 111284,515, 13 pages.
European Patent Office, Decision to Grant dated May 6, 2008 in European Patent Application No. EP04027855.8-2310/1661592,2 pages.
European Patent Office, European Search Report dated Aug. 10, 2007 in European Patent Application No. EP07010455.9-231O, 7 pages.
European Patent Office, Translation of European Search Report dated Apr. 20, 2005 in European Patent Application No. EP04027855.8, 4 pages.
European Search Report dated May 13, 2011 in related European Application No. 10194070.8.
European Search Report dated May 13, 2011 in related European Application No. 10194071.6.
European Search Report dated May 13, 2011 in related European Application No. 10194069.0.
European Search Report dated Dec. 1, 2015 in related European Application No. 15171240.3.
Office Action Dated Mar. 30, 2015 in corresponding Chinese Patent Application No. 201180067014.X.
Office Action Dated Nov. 26, 2015 in corresponding Chinese Patent Application No. 201180067014.X.

\* cited by examiner

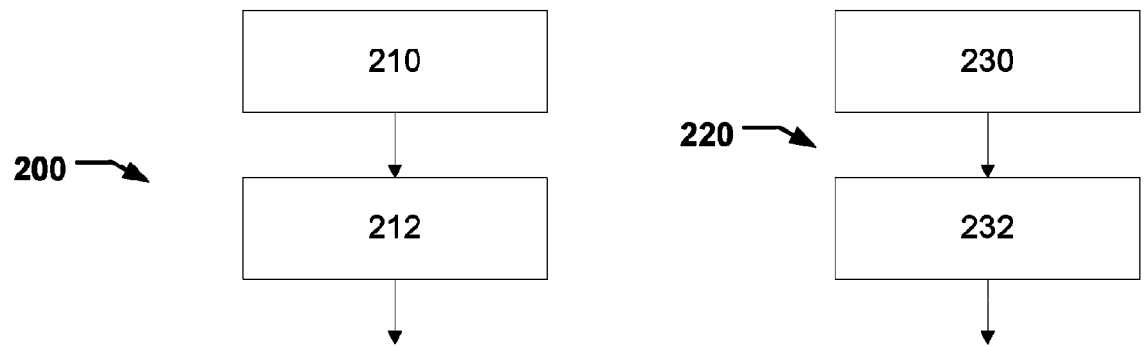
Fig. 9a  Fig. 9b
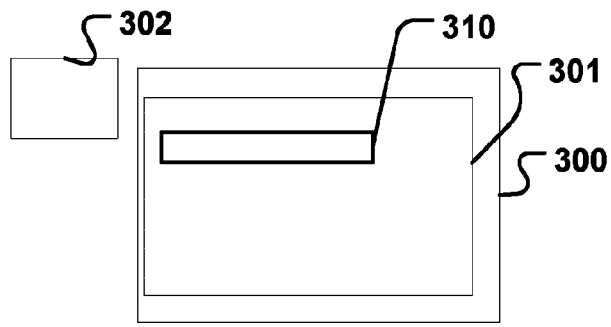
Fig. 10a
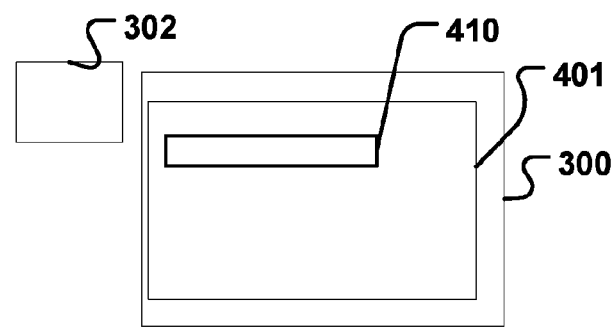
Fig. 10b

METHOD AND SYSTEM FOR FILLING AND VENTING A DEVICE FOR EXTRACORPOREAL BLOOD TREATMENT, WITH STEPPED FLOODING OF A FILTER

FIELD OF THE INVENTION

The present invention relates generally to a method and devices for carrying out extracorporeal blood treatment, and to a system and kit comprising such devices. In particular, the present invention relates to systems, such as heart-lung machines, and associated devices for extracorporeal blood treatment, such as patient modules, and associated venting methods.

BACKGROUND OF THE INVENTION

Before a heart-lung machine can be used, it has to be prepared such that the patient can be connected quickly and safely to the system. This requires a machine in which the blood-conveying components are vented (also called "de-aired") by a filling liquid. The filling procedure is also called "priming" of the machine.

Air inclusions or released quantities of air can, during later use on the patient, cause air embolisms and, in the worst case, death.

Components and hose systems in conventional heart-lung machines are hitherto for the most part prepared for use by being filled and vented manually. The preparation is performed, for example, by partial filling of components, manual clamping of hose lines, "beating out" of air bubbles, tilting of components, or cyclical driving of the blood pumps. Components such as hoses, connectors and reservoir have to be vented in addition to components such as oxygenator, filter and blood pumps. When venting a conventional heart-lung machine by filling it, the filling procedure has to be carried out by experts (cardio technicians). This applies also to regular operation. By means of the manual interventions described above, the system is made ready for use. In some systems, the filling procedure takes place semi-automatically but nevertheless requires trained personnel and/or cardio technicians, who perform the filling procedure. In the semi-automatic method, the operator partly has to clamp hoses, initiate pump actions, etc.

Generally, these manual interventions are complicated and cost-intensive in terms of personnel. These manual interventions are also susceptible to error and are difficult to document.

The use of the manual interventions, particularly in emergency situations, causes difficulties for the patient, who is reliant on a rapid start-up of the heart-lung machine. In addition, the costs and the time that are needed for the intervention increase.

The European patent specification EP 1,661,592 B1 by Lifebridge Medizintechnik AG describes a portable heart-lung machine with semi-automatic filling. These portable heart-lung machines consist of a base station and of a control module with attached patient module. EP 1,661,592 is herewith incorporated by reference in its entirety and for all purposes. The patient module contains the blood conveying components and is disposed of after use by separation from the control module. The bloodconveying components include the blood pump, in the form of a centrifugal pump, a reservoir with filling level sensors, an arterial filter, an oxygenator, various connecting hoses and bypasses, and also sensors for detecting air and gas bubbles and for measuring pressure and flow.

In the portable heart-lung machine that is described in EP 1,661,592 B1, the components are filled and vented by manual rotation of the complete unit through 90° to a filling position. In the filling position, an automatic method is then initiated that permits filling. After the filling procedure, the unit is rotated back through 90° to a filled operating position. By the rotation to the operating position and by a method for automatic detection and elimination of air bubbles, the system is brought to the operating state.

However, for the rotation movement during venting, an additional mechanical rotary holder is needed in order to move the control module with the patient module from the operating position to the filling position and back again.

Moreover, in the manual and also in the semi-automatic systems, there is the danger of air inclusions being overlooked or undetected despite visual inspection of the components.

US Patent application number US2008/171960 of the same applicant as the present applicant, which hereby is incorporated by reference in its entirety for all purposes, an apparatus is disclosed for making extracorporeal blood circulation available, in a particular a heart-lung machine, comprising a venous connection and an arterial connection, between which a blood reservoir, a blood pump and a bubble detector for the detection of air bubbles are provided, with, downstream of the bubble detector, an arterial line leading to the arterial connection via an arterial clamp and a bypass leading via a bypass clamp back into the blood reservoir which is connected to a pump extracting air from the blood reservoir. In addition, a method is disclosed of operating such an apparatus. In WO 2005/065743 an EXTRACORPOREAL BLOOD CIRCUIT PRIMING SYSTEM AND METHOD are disclosed. A disposable, integrated extracorporeal blood circuit is disclosed that is employed during cardiopulmonary bypass surgery performs gas exchange, heat transfer, and microemboli filtering functions. A manual priming method is described.

Hence, there is a need to provide for improved priming methods and systems allowing for such improved priming. Advantageously, the priming should be done automatically.

Therefore, an aim of the disclosure is to ensure that a heart-lung machine can be vented fully automatically by filling, without input by the operator, and thus made ready safely for use. No manual interventions for venting should be performed on the components in the patient module between starting up the machine (initialization, manual attachment of various hose lines and manual attachment of the filling liquid) and the attachment to the patient. Moreover, the time needed for the venting method is intended to be further reduced by eliminating the previously required rotation of the base module for the venting procedure. Thus, the system is made rapidly available for use, especially for short-term emergency use.

It is therefore desirable to make available a method for preparing and venting a heart-lung machine in the form of a portable heart-lung machine, which method can take place without intervention of the operator. It is desirable in particular that, after the attachment of the filling liquid and the attachment of the table line, the filling procedure should be started manually and proceed fully automatically.

Components that are difficult to vent, such as a blood pump and an arterial filter, are preferably to be made available in such a way that, in the venting method, the air in the components can advantageously be purged and escape. Documentation of the venting procedure should be made possible by the components and method.

SUMMARY OF THE INVENTION

An object of the disclosure is to overcome the abovementioned disadvantages of the conventional methods and devices and to provide an advantageous solution.

The abovementioned object is achieved by the device, systems, methods or computer programs of the invention having the characterizing features of the attached independent claims.

Reliable filling, even during transport, increases the range of possible applications of the system and methods described hereinafter.

Accordingly, embodiments of the present invention preferably seek to mitigate, alleviate or eliminate one or more deficiencies, disadvantages or issues in the art, such as the above-identified, singly or in any combination by providing the described methods and devices have at least the advantages set forth below.

A method is provided for preparing and venting in a device for extracorporeal blood treatment, such as a heart-lung machine, preferably in the form of a portable heart-lung machine, can proceed without intervention of the operator. Only the preparation and initiation of the procedure are necessary. The remainder of the procedure takes place automatically and is monitored. After the attachment of the filling liquid and the attachment of the table line, the filling procedure is started manually and then takes place fully automatically.

The system for extracorporeal blood treatment, such as preferably a heart-lung machine, can be filled not only in a stationary environment but also during transport.

Air can be purged and escape from components of the device for extracorporeal blood treatment that are difficult to vent, such as the blood pump and the arterial filter, by virtue of the design and arrangement of the components and the venting method.

It is possible to monitor and record the venting procedure in an electronic protocol. The most important states of the system can be stored there. These include, for example, the state of clamps, times, sensors for parameters such as pressure, flow, air bubble detection.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIGS. 9a and 9b show schematic diagrams of the steps of various methods; and

FIGS. 10a and 10b show a schematic diagram of various computer programs for carrying out methods.

DETAILED DESCRIPTION OF THE INVENTION

Figure 1:
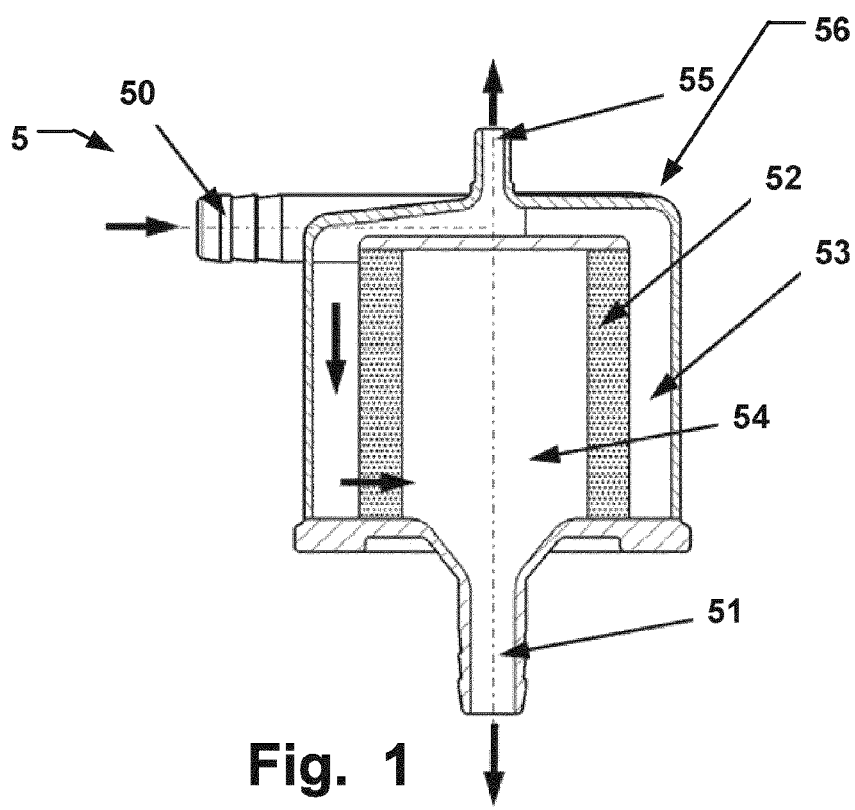
FIG. 1 shows across-sectional view of an arterial filter in a normal filling direction.

While the invention will be described in different embodiments and with the description of different methods for carrying out the invention, a person skilled in the art will appreciate that these embodiments are only illustrative, non-limiting examples of numerous forms that the present invention can take. The device for extracorporeal blood treatment is preferably arranged in a heart-lung machine. Other applications may for instance be in dialysis machines or the like in other embodiments.

More precisely, the described embodiments of the devices and of the system of the present invention are suitable for carrying out an automatic venting method.

Several examples of such methods for carrying out venting in association with the filling of a heart-lung machine are described below in detail.

As has been mentioned above, in the portable heart-lung machine described in EP 1,661,592 81, the components are filled and vented by manual rotation of the complete unit through 90° to a filling position. After the filling procedure, the unit is rotated back through 90° to a filled operating position.

The filling step serves to vent the components located in the patient module and is carried out by a 90° rotation movement of the control module with the patient module on the base station. When the control module with the patient module is located in the filling position, the blood pump pumps the filling liquid from an attached infusion bag into the system via the reservoir in a time-controlled manner. In this way, the components are filled with the filling liquid, and the air located therein is led out. For the subsequent use, the control module with the patient module is rotated back to the operating position, and the venting of the components is continued in the operating position for a defined time by further pumping of the filling liquid.

The rotation to the filling position, and therefore the venting of the system in this position, is required by two components, namely the pump head of the blood pump (centrifugal pump) and the arterial filter.

The pump head is arranged in the system in the operating position in such a way that the outlet of the pump points downwards and, therefore, any air possibly entering during operation rises inside the head, collects there and cannot pass into the circulation system. Were filling to take place in the operating position, the air in the upper area of the pump head would not be able to escape. For this reason, the system is rotated through 90° to the filling position, in order to allow the air to escape via the inlet of the pump head and therefore to ensure air-free filling.

The arterial filter is arranged in the system in the operating position in such a way that, because of its structure, the outlet points downwards and the inlet is arranged laterally at the top of the filter. If the filter is filled in the operating position from the inlet side (unfiltered side), the filling liquid crosses from the unfiltered side to the filtered side and the filter fills up. On the filtered side, in the inner filter area, the filling can lead to air inclusions in the upper area and also in the lower area. Air inclusions at the lower outlet area of the filter can break away during operation and thus pass into the circulation. By contrast, if the filter is first filled from the venting line (purge line) arranged at the top of the filter and then from the inlet side in the filling position (horizontal), the air in the filter can be displaced. The rest of the air remaining in the filter is removed from the filter via the venting line after the rotation to the operating position (see FIG. 1).

Without a rotation of the system through 90°, difficulties could hitherto arise in the venting of the blood pump and of the arterial filter. It was hitherto possible for air bubbles to accumulate in one or more of the components.

As regards the filter, it was also hitherto possible, during filling of the filter, for the membrane structure of the filter to be "closed" by the surface tension of the filling liquid, thereby making venting impossible. The air could not escape through the wetted membrane.

Moreover, the rising air from the hose mounted at the output of the filter collected in the outlet area of the filter. The air inclusion was not able to rise through the liquid flowing in from the input side and was continuously "entrained" in the direction of the filter outlet and broken up.

In principle, air bubbles could still be forced through a wetted membrane at pressures higher than the capillary forces. In practice, however, this is not feasible for several reasons. The reservoir might be destroyed, for example. The filter might also be affected. The pump might become overloaded and fail. In addition, a pressure higher than the maximum operating pressure of the system would be needed, which could lead to leakages. Alternatively, components could be used that permit higher operating pressures. However, these are much more expensive and therefore not an alternative on the market.

In some embodiments of the invention, the pressure is briefly increased at the end of the filling procedure, by means of the blood pump being operated at an increased pump speed. The pressure in the system is chosen such that it is below but close to the maximum operating pressure.

The abovementioned disadvantages of the prior art are avoided by embodiments of the invention. Fully automatic filling with venting is thus made possible without rotation of the system through 90°. This is explained in detail below.

The extracorporeal blood treatment system described in embodiments consists of a control module with attached patient module. The automatic hose clamps, the blood pump drive and the evaluation and control electronics are located in the control module. The patient module is a device for extracorporeal blood treatment. The components conveying the circulating blood are located in the patient module. The system is thus constructed in two parts. The operating position of the patient module is also its filling position. A rotary holder is dispensed with.

The components of the patient module that are shown in FIGS. 5 to 8 are, despite the schematic depiction, in their actual horizontal position relative to one another. This applies in particular to the reservoir 2, the blood pump 6, the oxygenator 3 and the filter 5. The particulars and significance of the positions of the components relative to one another are now explained in more detail by way of a number of embodiments.

Flow directions are illustrated in the diagrams by bold arrows on the corresponding lines, hoses or components.

Figure 5:
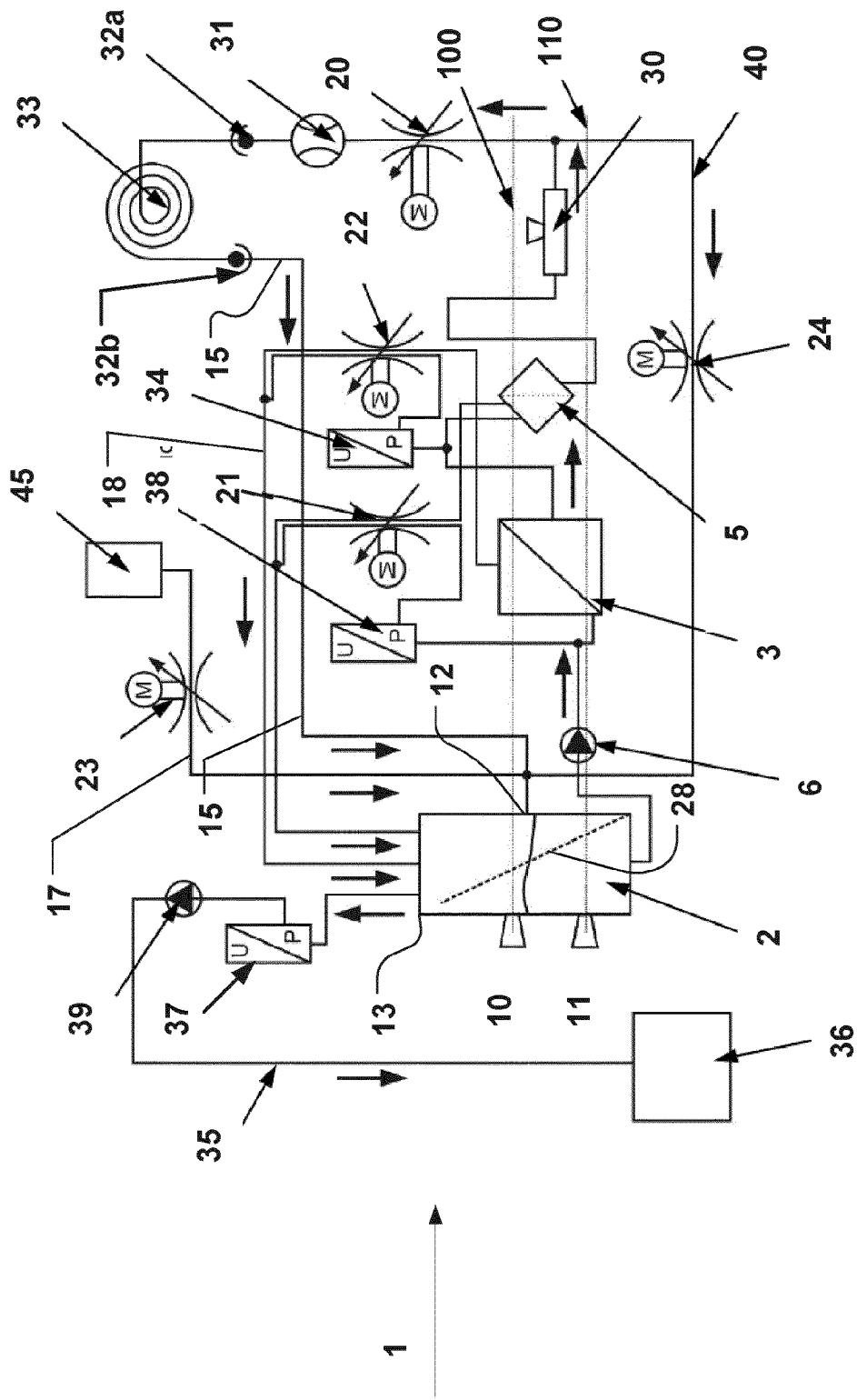
FIG. 5 shows a schematic overview of a circulation system for method 1.

FIG. 5 shows a circulation system. The circulation is constructed as follows: starting from the venous side, the venous line 15 ends in a reservoir 2 with screen 28.

Connected to the venous line 15 is a volume dose line 17 through which filling liquid from a storage container 45 and, optionally, a liquid supplied during use can be introduced into the circulation. This volume dose line 17 to the venous line 15 is controlled via a third hose clamp 23 (HC3).

The hose clamps described herein are general controllable valves for fluid lines. Fluid is understood as a liquid, such as blood or blood substitute, or a gas, such as air.

The reservoir 2 has an input 12 from the venous line 15 and a roller pump 39 with hose clamp function attached to the upper part 13 of the reservoir for the purpose of venting the reservoir 2, as described in the European patent specification EP 1,705,375 81, which is incorporated herein by reference in its entirety and for all purposes.

The reservoir 2 is equipped with an upper filling level sensor 10 and a lower filling level sensor 11. The reservoir comprises a screen 28, which separates the inlet area and outlet area across ⅘ of the surface of the reservoir.

The reservoir 2 also has, in the lower area, an output to a blood pump 6.

Figure 3:
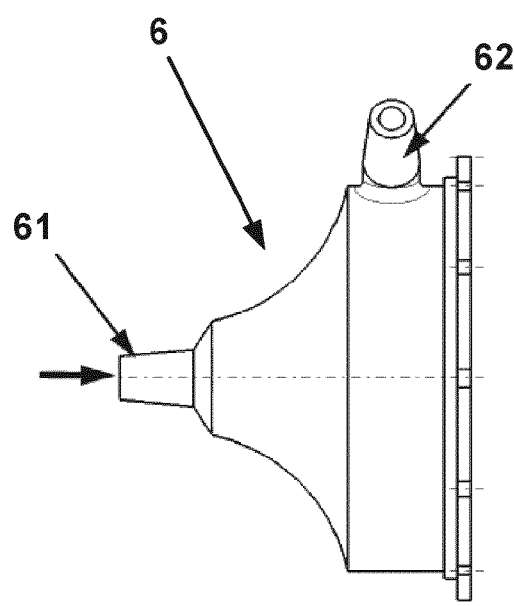
FIGS. 3 and 4 show schematic views of a blood pump.
Figure 4:
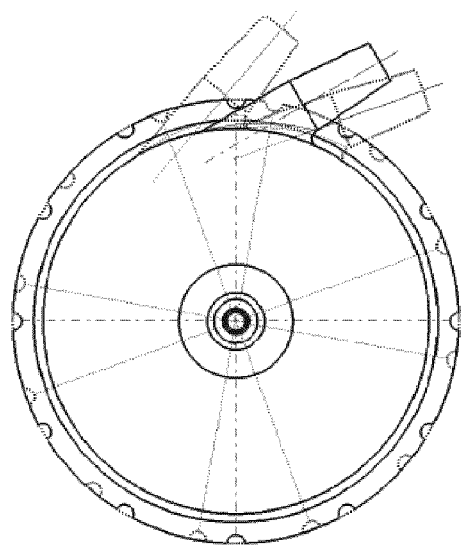

The blood pump 6 is preferably a centrifugal pump, as shown in FIGS. 3 and 4. The outlet 62 of the blood pump 6 is directed tangentially upwards. The inlet 61 of the blood pump 6 is arranged axially. In order to achieve the venting effect, the pump head can be rotated from the perpendicular position about 10° clockwise and about 20° counterclockwise as illustrated in FIG. 4.

The blood pump 6 downstream of the reservoir 2 has the axial inlet 61 attached to the reservoir 2, and the tangential outlet 62 is connected to the venous side of an oxygenator 3.

From an arterial attachment of the oxygenator 3, a liquid line, for example a hose, runs to an arterial filter 5. The oxygenator 3 also has attachments for an oxygen supply (not shown), and attachments for a hyperthermia device for controlling the temperature of the liquid in the circulation system (not shown). The oxygenator 3 also has an attachment for a venting line 18, which is connected separably to the upper part of the reservoir via a second hose clamp 22 (HC2).

Figure 2:
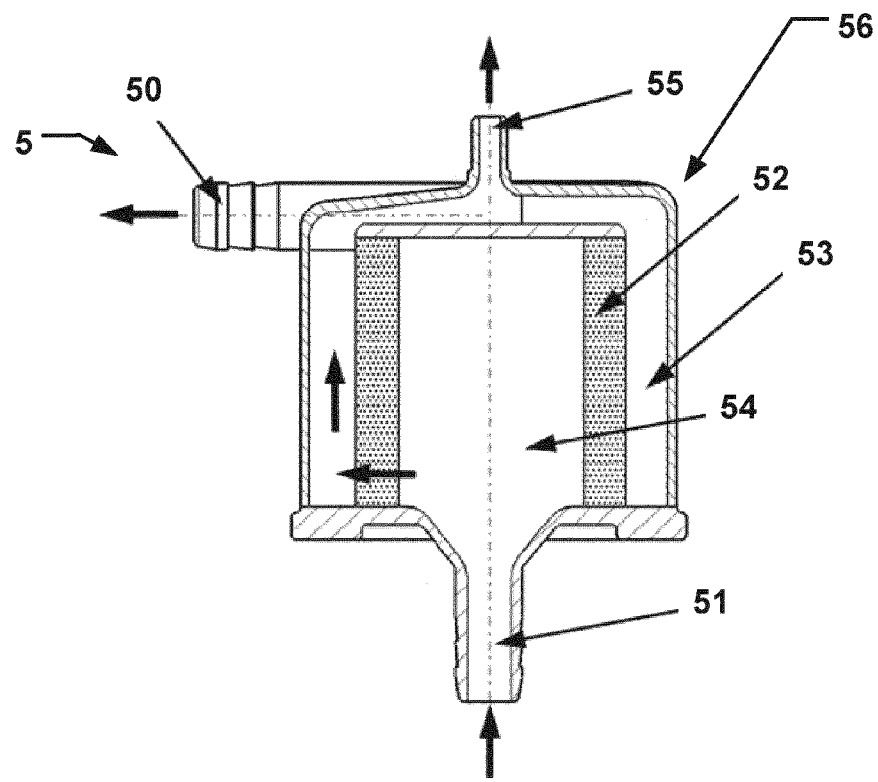
FIG. 2 shows across-sectional view of an arterial filter in a retrograde filling direction.

FIGS. 1 and 2 show an arterial filter 5 in different states. In addition to an outlet 51 to the arterial side, the arterial filter 5 also has a venting line 55 mounted on the upper part of the filter and leading to the upper part 13 of the reservoir, which venting line 55 can be clamped shut by a first hose clamp 21 (HC1). The filter has an unfiltered side 53 and a filtered side 54.

Arranged downstream of the arterial filter, there is an air bubble sensor 30 which, upon detection of air bubbles, activates a downstream quick-action hose clamp 20 (QAHC). Such a QAHC 20 is described in the European patent specification EP 1,698,371 B1, which is herewith incorporated by reference in full and for all purposes.

When an air bubble is detected by the bubble sensor, the QAHC 20 closes the arterial line 42 and opens a fourth hose clamp 24 (HC4) for a bypass 40, such that the liquid is pumped round the circuit until the detected air bubble is no longer located in the circulation of the patient module 1. Pressure and 20 flow sensors 34, 37, 38 are likewise integrated in the circulation. Before the system is vented, a table set 33 is attached to the venous attachment 32b and to the arterial attachment 32a, which table set 33 closes the circulation and is filled too during the venting. A patient is not attached to the circulation during the filling procedure.

The components in the patient module 1 are arranged in their positions as follows.

The reservoir 2 is installed in a 45° inclined position. However, it can also stand vertically in the system. The maximum filling level 100 of the reservoir 2 is regulated via the upper filling level sensor 10. During the filling procedure, the liquid level in the patient module 1 can thus be regulated such that it is located below the top face 56 of the arterial filter 5. This arrangement avoids a situation where the filter 5 is filled completely with liquid and the upper part of the membrane of the filter element 52 of the filter is thus wetted with filling liquid. Air inclusions can pass through the still "open", unwetted and therefore gaspermeable upper areas of the membrane of the filter 5 and escape.

The top face of the oxygenator 3 lies below or at the same height as the top face of the filter 5. The blood pump 6 on the reservoir 2 is located below the maximum filling level of the reservoir, below the horizontal position of the upper filling level sensor 10. The blood pump 6 can also be arranged below the lower edge of the reservoir 2. The liquid-conveying parts of the pump 6 are thus always located below the upper filling level sensor 10. The filling liquid can therefore pass merely by gravity from the filling liquid container 45 and through the tangential outlet 62 of the pump 6 to the downstream components. There is no danger of an air inclusion in the pump 6.

The patient module 1 for a heart-lung machine is provided with a support structure, which ensures the spatial arrangement of the components relative to one another. Thus, the patient module 1 contains a blood circuit with a blood pump 6, an oxygenator 3 with a top face, a filter 5 with a top face, and a reservoir 2. In the operating position of the patient module, the components are arranged in a horizontal position relative to one another in the support structure. The top face of the oxygenator 3 lies below or at the same height as the top face of the filter 5. The liquid-conveying parts of the blood pump 6 are located below the horizontal position of an upper filling level sensor 10 of the reservoir 2 and are thus located below the maximum filling level of the reservoir 2. The top face of the filter is higher than the upper filling level sensor of the reservoir. Thus, a partial filling of the filter 5 can be controlled, which permits an advantageous venting of the blood circuit.

In one embodiment, the filter 5 of the patient module has a venting line attached to the top face, wherein an attachment point for the venting line is higher than the upper filling level sensor 10.

The first controllable valve 21 (HC1) is arranged in the venting line of the filter. A control unit 302 (FIGS. 10a and b) of the heart-lung machine is configured such that, after the response of the upper filling level sensor 10, the first controllable valve 21 (HC1) is at least partially closed. The lower edge of the reservoir 2 has a lower edge, and the blood pump 6 lies below the lower edge or below a horizontal level of the lower edge of the reservoir (not shown). Alternatively, the blood pump 6 lies at the height of the lower third of the reservoir.

The patient module can have an additional fifth hose clamp 25 (HC5). The HC5 25 is arranged in the venous line 15 between volume dose inlet and reservoir 2 and a feed point of the filling liquid, which is higher than the reservoir, the filter and the oxygenator (see the embodiment of the patient module in FIG. (6).

The heart-lung machine has a control unit for the fully automatic filling and venting of a patient module according to the invention. The control unit, for filling and venting the patient module, is configured to close the first controllable valve 21 (HC1), which is opened after the start of the filling procedure for the venting line of the filter 5, and after the response of the upper filling level sensor 10 in the reservoir 2, in order to control the active filling of the filter 5. The filling liquid from the filling liquid container 45, located higher than the patient module and connected thereto, thus flows by gravity via the venous side of the system into the reservoir 2 and onwards into the blood pump 6 located at the lower end of the reservoir 2 and then onwards into the filter 5.

Thus, an air cushion is created in the filter by the closed first controllable valve 21 (HC1) and the therefore closed venting line. The air cushion damps the flow behaviour of the incoming filling liquid. A first speed of the blood pump is chosen by the control unit 302 such that as low filling of the filter 5 from the inlet side takes place, and this filter is only partially filled, and an upper area of the filter membrane 52 remains unwetted by the filling liquid and thus remains air-permeable for the further filling and venting procedure.

Figure 6:
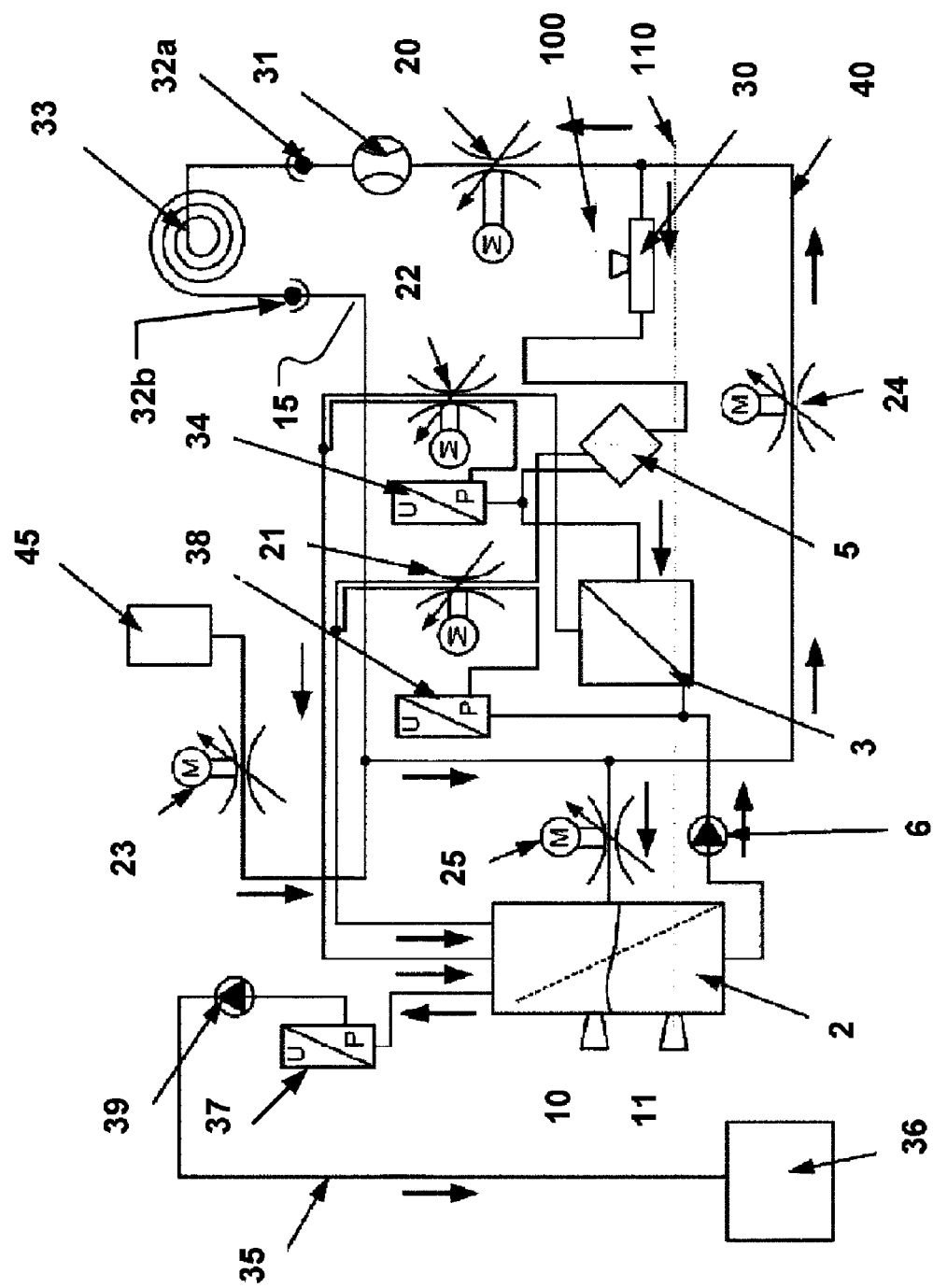
FIG. 6 shows a schematic overview of a circulation system for method 2 with retrograde filling.

Moreover, in embodiments such as in FIG. 6, the control unit is configured to close the fifth controllable valve 25 (HC5) when the filling liquid in the reservoir is detected by the lower filling level sensor 11. As a result of this, a venous connection between volume dose inlet and the reservoir 2 is separated by means of the fifth controllable valve 25 (HC5). The filling liquid will now flow only through the venous line via the bypass 40 to the arterial filter 5. Thus, by means of the pressure applied, the filter 5 is filled in a retrograde manner from the outlet side by gravity.

The patient module can comprise an air bubble sensor 30. The air bubble sensor is arranged so as to detect air in the system. When an air bubble is detected by the sensor, the control unit is configured to switch off the table set by means of the quick-action hose clamp (QAHC) 20. The fourth controllable valve 24 (HC4) is opened again and the air in the system is led off via the reservoir.

The patient module provided in the heart-lung machine, allows for the filling and venting procedure to be carried out during transport of the machine. Transport is an operative condition of such a machine that provides for different challenges than stationary operation. For instance, space is limited, e.g. in an ambulance or a helicopter. Moreover, access to operating personel may be limited. This makes it so important that automatic priming is provided in the reliable manner described herein.

The control unit 302 is adapted to carry out the venting fully automatically and, after the start of the venting procedure, to carry out all the sequences automatically until the venting procedure has been completed.

After the start, the volume dose line is opened by the third controllable valve 23 (HC3), and, in doing so, the second controllable valve HC2 22, the fourth controllable valve 24 HC4 and the quick-action hose clamp QAHC 20 and also the roller pump 39 with hose clamp function are opened.

In some embodiments, the heart-lung machine is adapted to record the filling and venting procedure and thus document the latter in readable form. For example, data such as the indexing positions of the controllable valves, filling levels of the reservoir, switch-on and switch-off times, the response of the air bubble sensor and other parameters such as pressure and flow can be stored in a storage unit. The control unit 302 can administer these data to and from the storage unit.

A non-transitory computer-readable storage medium encoded with programming instructions, said storage medium being loaded into a computerized control system of an apparatus, and said programming instructions causing said computerized control unit to control priming of apparatus prior to connection to a patient are described now.

A computer program 301 for controlling the filling and venting of a patient module is shown in FIG. 10a. In a heart-lung machine, without attached patient, the computer program 301 is executed by a computer unit, such as the control unit 302. The computer program is implemented on a computer-readable storage unit. During said filling and venting, a filling liquid from a filling liquid container located higher than the patient module flows by gravity via a venous side of the system into a reservoir and flows onwards into a blood pump located at the lower end of the reservoir. The computer program comprises code segments, wherein one code segment 310, first opens a controllable valve for a venting line of a filter and, after a response from an upper filling level sensor in the reservoir, is closed. The computer program 301 is preferably suitable for carrying out the below-mentioned embodiment of a "first method." A kit for a heart-lung machine comprises a patient module, a table set 33, and a filling liquid container 45 for a filling liquid.

Another computer program 401 for controlling the filling and venting of a patient module is shown in FIG. 10b. In a heart-lung machine, without attached patient, the computer program is executed by a computer unit, such as the control unit 302. The computer program 401 is implemented on a computer readable storage unit. During said filling and venting, a filling liquid from a filling liquid container located higher than the patient module flows by gravity via a venous side of the system into a reservoir and flows onwards into a blood pump located at the lower end of the reservoir. The blood pump is located below a lower filling level sensor of the reservoir. The computer program comprises code segments, wherein one code segment 410, upon detection of the filling liquid in the reservoir by the lower filling level sensor, closes the fifth controllable valve 25 (HC5), as a result of which, a venous connection between volume dose inlet and the reservoir is separated, and the filling liquid flows only through the venous line via a bypass to an arterial filter, and, by means of the pressure applied, the filter is filled in a retrograde manner from the outlet side by gravity. The computer program 401 is preferably suitable for carrying out the below-mentioned embodiment of a "second method."

FIG. 9a shows a schematic diagram of the steps of a first method, and FIG. 10a shows a schematic diagram of a computer program for carrying out the first method.

FIG. 5 shows the above-explained circulation system for the first method 200, as shown in FIG. 9a. This method 200 is a method for filling and venting a patient module in a heart-lung machine. A patient is not attached thereto during the filling procedure. The method comprises the step 210, in which a filling liquid from filling liquid container located higher than the patient module flows by gravity via a venous side of the system into a reservoir and flows onwards into a blood pump located at the lower end of the reservoir. The first controllable valve 21 HC1 is opened for the venting line of the filter 5. In a further step 212, the first controllable valve is closed after a response from an upper filling level sensor in the reservoir.

After the start of the venting procedure, all the process steps run automatically until the venting procedure is completed. After the start, the HC3 23 opens the volume dose line. The filling liquid from the filling liquid container 45 located higher than the patient module flows by gravity via the venous side of the system into the reservoir 2 and flows onwards into the blood pump 6, in the form of a centrifugal pump, located at the lower end of the reservoir 2. The HC2 22, HC4 24 and the QAHC 20 and the roller pump 39 with hose clamp function are opened. The HC1 21 for the venting line of the filter 5 is likewise opened, and it is closed only after the response of the upper filling level sensor 10 in the reservoir. The roller pump 39 is likewise closed after the response of the upper filling level sensor 10 in the reservoir, and in this way no more air can escape through the venting path 35 to the collecting bag 36, and the filling of the reservoir 2 via the filling liquid container 45 is stopped. Depending on the state of filling of the reservoir 2, the roller pump 39 is opened or closed. When the filling liquid reaches the upper filling level sensor 10 in the reservoir 2, it is assumed that the downstream components are filled by gravity with filling liquid. After the upper filling level sensor 10 has been reached, the HC1 21 is closed in order to ensure the continued active filling of the filter 5. An advantageous air cushion forms.

Because of the structure of centrifugal pumps, a liquid has to be present in the pump in order to permit the active delivery of liquids. There is no suction behaviour for air in the pump head, as in a diaphragm pump.

The blood pump 6 located in the patient module is oriented in its installation position in such a way that it can be filled by gravity with filling liquid through the upwardly directed tangential outlet 62 and through the axial inlet 61 (see FIG. 3). The air rises in the blood pump 6 and is led off via the outlet 62.

After gravitational filling has taken place, a start/stop movement of the pump 6 ensures that the air located in the blood pump is transported to the outlet 62 and led off. During a stop of the pump, the air can rise in the direction of the pump outlet 62, and it can be transported off by starting the blood pump 6.

The arrangement of reservoir 2 and blood pump 6, namely below the maximum filling level of the reservoir 2, ensures that the blood pump 6 is filled by gravity and, in this way, there is always liquid in the blood pump 6 during the venting procedure.

The blood pump 6 filled with filling liquid is operated at periodic intervals at a low speed, depending on design and delivery rate. The filling liquid is conveyed from the reservoir 45 into the oxygenator 3 and onwards into the arterial filter 5. By means of the slow filling of the filter 5 from the inlet side 50, the filter is only partially filled. The upper area of the filter membrane 52 remains unwetted by the filling liquid and is therefore still air-permeable. Any air inclusions can cross from the filtered side 54 to the unfiltered side 53 and be led off. The introduced filling liquid passes through the lower part of the filter membrane to the filtered output side 54 and fills the downstream circulation system. The air from the hose attached to the filter output side 54 can escape into the filter 5 and to the unfiltered side 53 through the unwetted part of the filter membrane 52.

Moreover, an air cushion forms in the filter 5 on account of the closed venting line, since the HC1 is closed, and the filling liquid located at the filter output. The air cushion advantageously damps the flow behaviour of the incoming filling liquid.

After a defined filling time at a low speed and thus a low delivery rate, the speed of the blood pump 6 is increased in steps to a constant value, and the bypass 40 is clamped by closure of the hose clamp HC4 24, and in this way the attached table set 33 has liquid passed through it and is vented.

In the following step, the HC4 24 is opened again and the speed of the blood pump 6 is further increased. By means of the further closure of the HC4 24 and a further increase of the speed and therefore an increase in the output rate of the blood pump 6, more liquid is passed through the table set 33 and the latter is further vented. During this, the HC1 21 is opened, i.e. the venting clamp of the arterial filter 5. The air remaining in the upper part of the filter can thus escape.

In order to vent the bypass again, the HC4 24 is opened again. If, in the last steps, air in the system is detected by the air bubble sensor 30, the QAHC clamps the table set 33 off, the HC4 24 opens, and the air in the system can be led off via the reservoir 2. By means of the filling level sensors in the reservoir 2, the liquid level is permanently monitored, so as to supply the system with sufficient filling liquid.

The venting procedure is recorded and thus documented in readable form. The indexing positions of the hose clamps, filling states of the reservoir, switch-on and switch-off times, the response of the air bubble sensor and other parameters such as pressure and flow can be stored.

Figure 7:
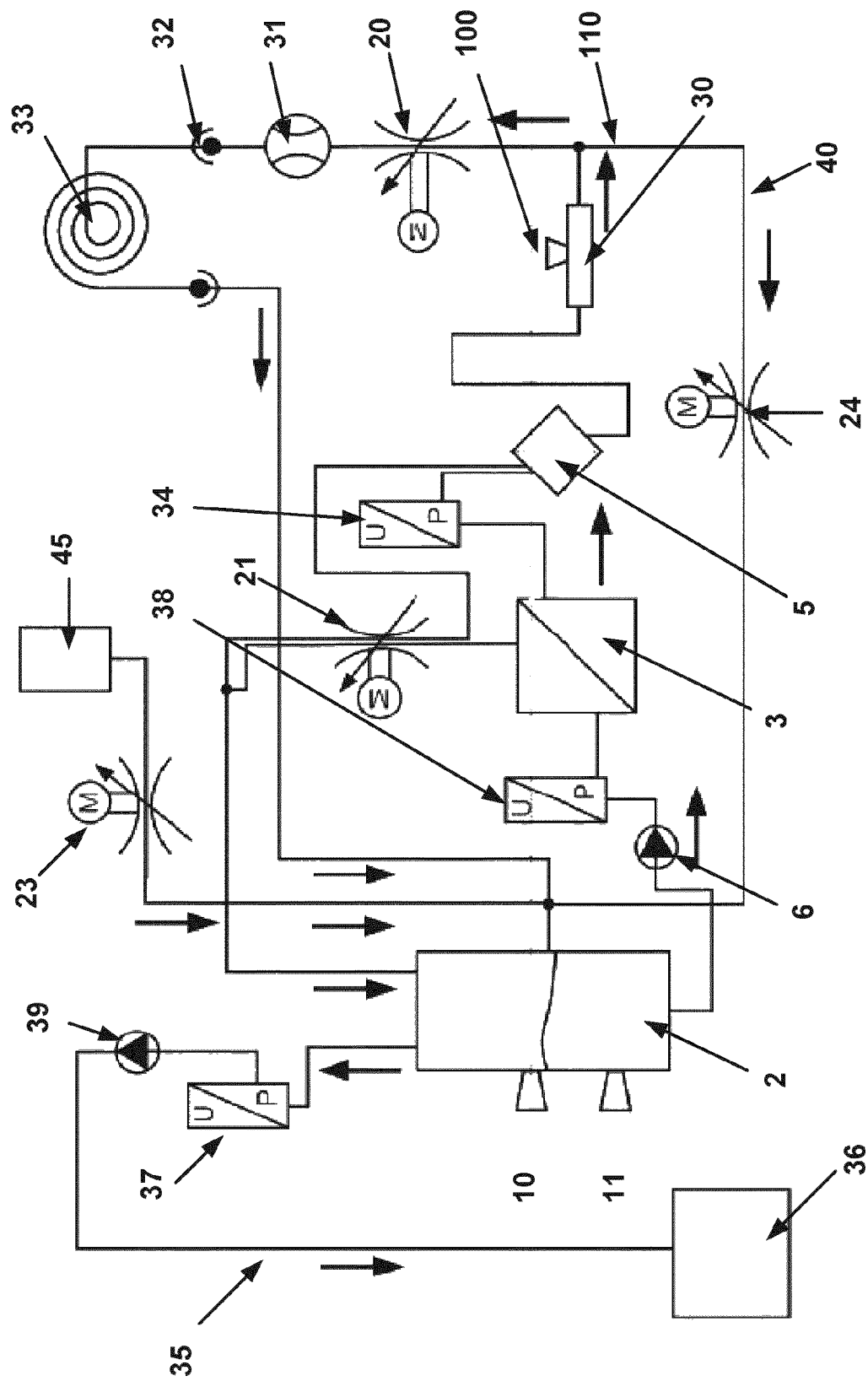
FIG. 7 shows a schematic overview of a circulation system for method 1 with integrated pressure measurement.

The venting procedure can also be carried out during transport or mobile use of the heart-lung machine. FIG. 7 shows a schematic overview of a circulation system for the first method 200 with integrated pressure measurement. The circulation system is like the one for the previously explained first method, but with four controllable valves, here hose clamps. The clamps HC1 21 and HC2 22 shown in FIG. 6 are here combined into one hose clamp 21 a by integration of the pressure measurement into the hose system between blood pump band oxygenator 3 and oxygenator 3 and filter 5.

FIG. 6 is a schematic overview of a circulation system for a second method 220 with retrograde filling. FIG. 9b is a schematic diagram of the steps of the second method 220. FIG. 10b is a schematic diagram of a computer program 401 for carrying out a second method.

The conditions are as in the first method, only with the blood pump 6 on the reservoir 2, which is located below the lower filling level sensor 11 of the reservoir 2. The blood pump 6 can also be arranged below the lower edge of the reservoir 2. An additional controllable valve, here the hose clamp HC5 25, is arranged in the venous line between volume dose inlet and reservoir 2 and a feed point of the filling liquid, which feed point is higher than the reservoir, the filter and the oxygenator.

The second method 220 is a method for filling and venting a patient module in a heart-lung machine, without attached patient. A filling liquid from a filling liquid container located higher than the patient module flows by gravity via a venous side of the patient module into the reservoir 2 and flows onwards into the blood pump 6 located at the lower end of the reservoir 2. The blood pump is located below the lower filling level sensor 11 of the reservoir 2.

When the filling liquid in the reservoir 2 is detected, the fifth controllable valve 25 (HC5) is closed by the lower filling level sensor 11. Therefore, by means of the fifth controllable valve 25, a venous connection between volume dose inlet and the reservoir 2 is separated. The filling liquid now flows only through the venous line via the bypass 40 to the arterial filter 5. By means of the pressure applied by gravity, the filter is filled in a retrograde manner from the outlet side 51 (see FIG. 2).

After the start of the venting procedure, all the sequences are carried out automatically until the venting procedure is completed. After the start, HC3 23 opens the volume dose line. The filling liquid from the filling liquid container 45 located higher than the patient module flows by gravity via the venous side of the system into the reservoir 2 and onwards into the blood pump 6, in the form of a centrifugal pump, located at the lower end of the reservoir. HC1 21, HC2 21, HC4 24, HC5 25 and the QAHC 20 and the roller pump 39 with hose clamp function are opened.

The filling liquid flows by gravity at the same time through the venous line into the reservoir 2 and via the bypass 40 in the direction of the output of the arterial filter 5. Because of its higher position of installation, the filter 5 cannot be filled, since the filling liquid flows off into the reservoir 2.

The blood pump 6 located in the patient module is oriented in its installation position in such a way that it can be filled by gravity with filling liquid through the upwardly directed tangential outlet 62 and through the axial inlet 61 (see FIG. 3). The air rises in the blood pump 6 and is led off via the outlet 62. As soon as the filling liquid in the reservoir 2 has reached the lower filling level sensor 11 in the reservoir, the downstream blood pump is filled completely with filling liquid.

The lower filling level sensor 11 detects the filling liquid in the reservoir, and HC5 25 is closed. The venous connection between volume dose inlet and the reservoir 2 is thus separated. The filling liquid can flow only through the venous line via the bypass 40 to the filter 5. By means of the pressure applied by gravity, the filter 5 is filled in a retrograde manner from the outlet side. In this way, in the filter, the air can escape from the filtered side to the unfiltered inlet side (see FIG. 2). The filling by gravity results in a gradual venting and filling of the filter 5. The air can escape through the venting line on the upper part of the filter, and the filling liquid can flow onwards to the oxygenator 3. Retrograde filling likewise takes place in the oxygenator 3. The air is led off through the venting line of the oxygenator.

In the next step, the HC5 25 is opened and the filling liquid flows into the reservoir 2 again until the upper filling level sensor 10 detects liquid. In this way, the blood pump 6 is activated and its speed is increased in steps up to a constant value. Moreover, the bypass 40 is clamped by closure of the hose clamp HC4 24, and liquid flows through the attached table set 33.

In the following step, the HC4 24 is opened again and the speed of the blood pump 6 is further increased. By means of the further closure of the HC4 24 and a further increase of the speed and therefore an increase in the output rate of the blood pump 6, more liquid flows through the table set 33 and the latter is further vented. The opened venting lines of the filter 5 and of the oxygenator, through HC1 21 and HC2 22, allow any air present in the components to escape to the reservoir 2.

By means of the closure of HC4 24 and QAHC 20, the venting lines of the oxygenator 3 and of the arterial filter 5 are again flushed in the last step of the venting procedure.

If, in the last steps, air in the system is detected by the air bubble sensor 30, the QAHC 20 clamps the table set off, the HC4 24 opens, and the air in the system can be led off via the reservoir 2.

By means of the filling level sensors in the reservoir 2, the liquid level is permanently monitored, so as to supply the system with sufficient filling liquid.

Figure 8:
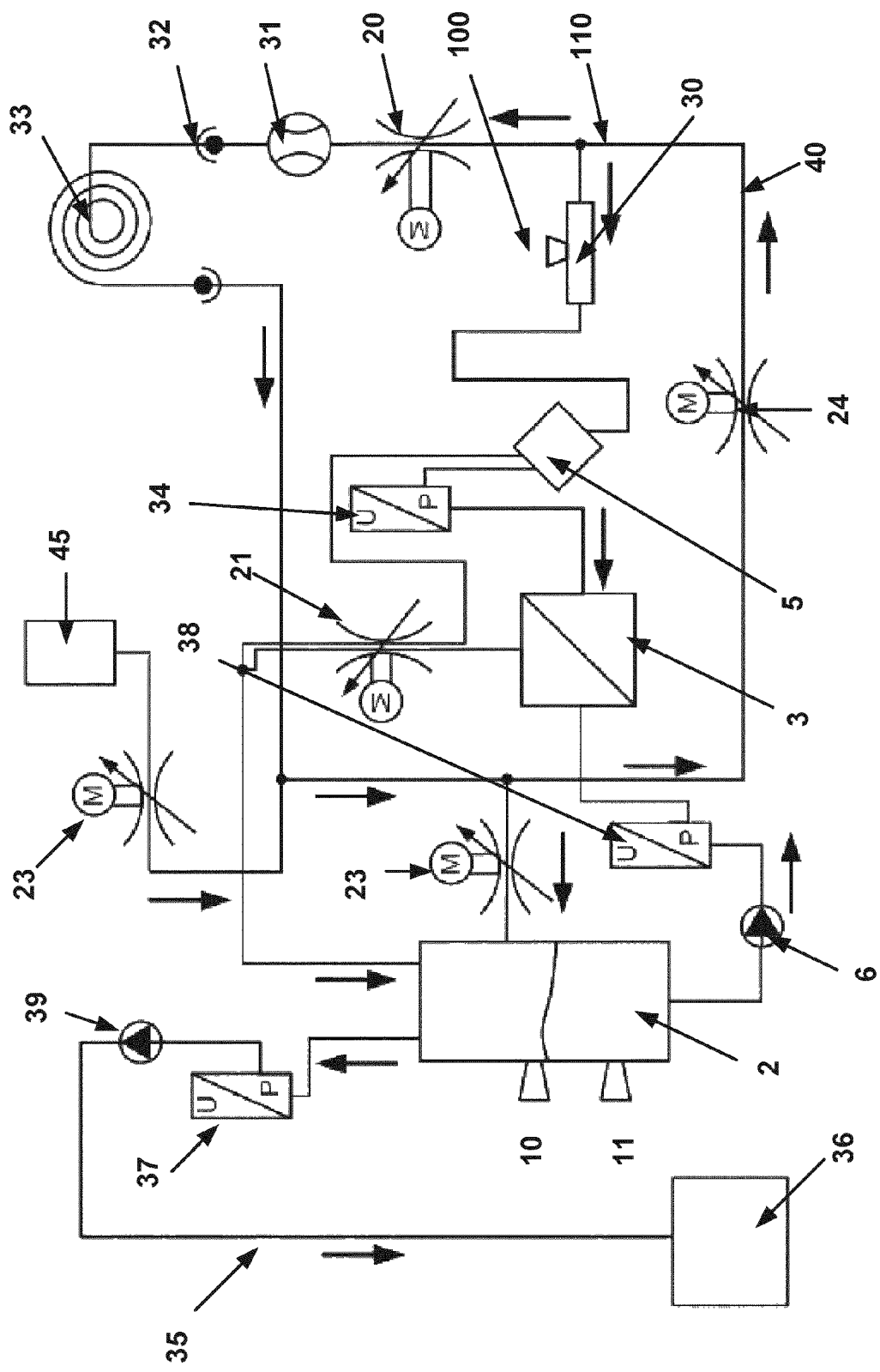
FIG. 8 shows a schematic overview of a circulation system for method 2 with integrated pressure measurement.

FIG. 8 is a schematic overview of a circulation system for the second method with integrated pressure measurement.

The circulation system is structured as described in FIG. 6 for the second method 220, but with only five hose clamps. HC1 21 and HC2 22 are combined into one hose clamp 21 a by integration of the pressure measurement into the hose system between blood pump band oxygenator 3 and oxygenator 3 and filter 5. The blood pump 6 is arranged below the lower edge of the reservoir.

The venting procedure is recorded and thus documented in readable form. The indexing positions of the hose clamps, filling states of the reservoir, switch-on and switch-off times, the response of the air bubble sensor and other parameters such as pressure and flow can be stored.

The venting procedure can also be carried out during transport or mobile use of the heart-lung machine.

After the filling and venting procedure, the patient is attached as follows. The patient is made ready during the filling procedure, with an arterial needle being introduced into the femoral artery and with a venous needle being introduced into the femoral vein of the patient. After the system has been filled, the table set filled with the system is separated (severed) at the middle and plugged without air inclusions onto the prepared needles and perfusion commenced.

A number of medical procedures can then be carried out on the patient. Examples of medical applications are, among others, an emergency use in acute heart failure (cardiogenic shock); heart support in order to avoid organ damage; lung failure (ARDS); high-risk interventions on the heart (PCI [stent], DAVI [heart valves]); support in beating-heart surgery (CABG [bypass operation on the eating heart]); perfusion of donor candidates for organ transplantation; temperature stabilization of hypothermic patients (warming the patient to body temperature); temperature control of the patient=>hypothermia, deliberate lowering of the body temperature, e.g. stroke.

An exemplary method of using the described heart-lung machine after priming is now outlined. First the heart-lung machine is primed, or filled, with a priming fluid such as sterile saline—preferably in a manner as described above. Once initiated, the priming can take place in an automated manner without human intervention. The machine is then switched from the filling (or priming) mode into an automated operational mode. Once primed, the machine is fluidly coupled to the circulatory system of the donor through a vein to the venous coupling of the machine and through an artery to the arterial coupling of the machine. The method may include the addition of drugs or other additives to the blood by way of the heart-lung machine. For example, an anticoagulant may be added to the blood to prevent clotting. The organs to be donated may be sustained until transplantation using the heart-lung machine or they may be sustained by the heart-lung machine, harvested, and transported separately before transplantation. The heart-lung machine may prevent decomposition of the organ(s) until shortly before transplantation of the organ to an organ receiver. The viability of one or more organs is maintained in the organ donor for subsequent transplantation. When the organ is ready to be implanted to the organ receiver, the donor body or harvested organ is disconnected from the heart-lung-machine.

In addition, or alternatively, one or more harvested organs may be kept alive by means of the heart-lung machine after harvesting. The organs may then be perfused during transport by the heart lung-machine. Organs in particular suitable for such transport after harvesting comprise, but are not limited to, the heart, lungs, liver, or limbs. However, this is under certain circumstances not feasible for some organs, such as eyes. Under such circumstances certain organs, such as eyes, are preferably sustained and kept from decomposing, by perfusing the entire body of a deceased, brain dead, or clinically dead organ donor.

In this manner, the method allows for one or more organs to be transported from one location to another location for transplantation. Transport is in particular facilitated by using the heart-lung machine in accordance with the afore described embodiments. The organs may be kept in a condition that allows to prevent a decomposition of the organ that would occur without interaction of the heart-lung-machine with the organ. Blood or a blood substitute liquid may be used in the method for perfusing the organ(s).

Another exemplary method of using the described heart-lung machine after priming is now outlined. The method priming, or filling, the heart-lung machine with a priming fluid such as sterile saline—preferably as described above. Once initiated, the priming can take place in an automated manner without human intervention. The machine is then switched from the filling (or priming) mode into an automated operational mode. When primed and operational, the machine is fluidly coupled to the circulatory system of the patient through a vein to the venous coupling of the machine and through an artery to the arterial coupling of the machine.

The heart of the patient may optionally be slowed or stopped, if necessary. The blood returned to the patient is enriched with oxygen. In some cases the blood temperature may be controlled to a body temperature below normal body temperature and above a temperature where organs may be damaged. Such a temperature is in the range of may today be achieved by placing the patient, or only the heart, during surgery in an ice bath. However, by controlling the blood temperature, and perhaps cooling the blood before reentering it into the patient via the venous vessel connection, is an elegant solution where the body temperature is much better controllable.

The method may include the addition of drugs or other additives to the blood by way of the heart-lung machine. For example, an anticoagulant may be added to the blood to prevent clotting. The valve replacement or valve repair is then performed during the medical procedure. The cardiac valve is either replaced by an artificial valve unit or the valve is repaired.

Valve repair may include positioning of an annuloplasty implant, a leaflet clip, or other medical devices suitable for repairing a defective cardiac valve. In this manner for instance regurgitation may be treated. Alternatively, or in addition, surgical methods may be performed where e.g. portion of leaflets are removed to correct a defective closure of the valve.

Valve replacement or valve repair is preferably performed in a minimal invasive way. Percutaneous access to the heart via introducers and catheters in the circulatory system is a suitable medical procedure for accessing the heart in the present context.

Valve replacement may comprise removal of a dysfunctional heart valve. Alternatively, or in addition, an artificial valve is positioned at the location of the dysfunctional valve needing replacement. If for instance a so called stent valve is used, the dysfunctional valve may not need to be surgically removed before positioning the artificial replacement valve.

The cardiac valves to be repaired or replaced are for instance the mitral valve or the tricuspid valve. When the valve replacement or repair is concluded, the medical procedure is about to be finished. The tools used to access the heart are removed. The introducer is removed and the wound is closed. When desired, the patient's heart is started again, if necessary, the patient is disconnected from the heart-lung machine, and the operation of the machine is terminated.

Another exemplary method of using the described heart-lung machine after priming is now outlined. The method according to the present invention comprises priming, or filling, the heart-lung machine with a priming fluid such as sterile saline—preferably as outlined above. Once initiated, the priming can take place in an automated manner without human intervention. When primed and operational, the machine is fluidly coupled to the circulatory system of the patient through a vein to the venous coupling of the machine and through an artery to the arterial coupling of the machine.

The heart of the patient may optionally be slowed or stopped, if necessary. The blood returned to the patient is enriched with oxygen. In some cases the blood temperature may be controlled to a body temperature below normal body temperature and above a temperature where organs may be damaged. Such a temperature range may currently be achieved by placing the patient, or only the heart, in an ice bath during surgery. Controlling the blood temperature, and perhaps cooling the blood before reentering it into the patient via the venous vessel connection, is an elegant solution whereby the body temperature and/or the heart temperature is much better controlled.

In the case of a coronary artery bypass graft a graft vessel, such as a segment of saphenous vein, an internal thoracic artery, or a radial artery is taken from the patient, a cannulae is sutured into the heart, and cardiopulmonary bypass using the heart-lung machine is initiated. The aorta is clamped and the heart is stopped and cooled to, for example, 29'C. One end of the graft vessel is sutured a coronary artery beyond a blockage to be bypassed. The heart is then restarted, the other end of the graft vessel is sutured to the aorta while the heart is beating, and the heart-lung machine is disconnected from the patient.

The method may include the addition of drugs or other additives to the blood by way of the heart-lung machine. For example, an anticoagulant may be added to the blood to prevent clotting while the heart is stopped.

In the case of percutaneous angioplasty or stent placement, a balloon is inflated inside a coronary artery to widen the passage or to expand a stent that will widen the artery and support the artery in a more open configuration to improve blood flow therethrough. The heart may be, but is usually not stopped for percutaneous angioplasty or stent placement, but the expansion of the balloon catheter inside the artery may cause the artery to rupture and necessitate emergency heart surgery. The heart-lung machine may be used in the event of such a complication or other complications that require the heart to be stopped or slowed. The heart-lung machine may be, but need not be, primed as a precaution before a possible complication.

A person skilled in the art will appreciate that changes and modifications can be made to the described examples without departing from the scope of the attached claims.

| List of reference signs | |
|---|---|
| 5 | filter |
| 51 | outlet |
| 52 | filter element |
| 53 | unfiltered side |
| 54 | filtered side |
| 55 | venting attachment |
| 56 | top face of filter |
| 6 | blood pump |
| 61 | axial inlet |
| 62 | tangential outlet |
| 1, 1a | patient module |
| 10 | upper filling level sensor |
| 100 | position of upper filling level sensor |
| 11 | lower filling level sensor |
| 110 | position of lower filling level sensor |
| 12 | input from venous line to reservoir 2 |
| 13 | upper part of reservoir |
| 15 | venous line |
| 17 | volume dose line |
| 18 | venting line for oxygenator |
| 2 | reservoir |
| 3 | oxygenator |
| 20 | quick-action hose clamp QAHC |
| 21 | hose clamp 1HC 1 |
| 22 | hose clamp 2HC 2 |
| 23 | hose clamp 3 HC 3 |
| 24 | hose clamp 4 HC 4 |
| 25 | hose clamp 5 HC 5 |
| 28 | screen in reservoir 2 |
| 30 | bubble sensor |
| 31 | flow sensor |
| 32a, b | connectors |
| 33 | table set |
| 34 | pressure gauge |
| 35 | venting line |
| 36 | collecting bag |
| 37 | pressure gauge |
| 38 | pressure gauge |
| 39 | roller pump |
| 40 | bypass |
| 42 | arterial line |
| 45 | storage container |
| 200 | method 1 |
| 210, 212 | method steps |
| 220 | method 1 |
| 230, 232 | method steps |
| 300 | storage medium |
| 301, 401 | computer program |
| 302 | processor, control unit |
| 310, 410 | program segments |

The invention claimed is:

1. A method for filling and venting a device for extracorporeal blood treatment, wherein said device comprises i) a control module having an automatic clamping or valving apparatus, a blood pump drive, and evaluation and control electronics, and ii) a patient module having a blood flow circuit which comprises a venous blood inflow conduit, a reservoir, an oxygenator, an air bubble detector, a filter, an arterial blood outflow conduit, and a blood pump; said method comprising the steps of:
   a) engaging the patient module with the control module;
   b) connecting the patient module to a source of filling fluid such that filling fluid gravity-flows into at least the reservoir and blood pump;
   c) entering, via a user interface, a command which initiates an automatic filling and venting process wherein the evaluation and control electronics include a control unit that is adapted to automatically control components of the patient module to fill and vent the blood flow circuit without requiring human intervention, said filling and venting of the blood flow circuit including a stepped flooding of the filter whereby the filter is initially partially filled with liquid such that a portion of the filter remains unwetted and air permeable during further filling and venting of the blood flow circuit and, thereafter, the filter is further filled with liquid such that the unwetted portion of the filter also becomes wetted; and
   wherein, after the system has been connected to a source of filling fluid and said command has been entered, the control unit automatically controls components of the patient module to effect said automatic filling and venting process, including the stepped flooding of the filter, without requiring other human intervention.

2. A method according to claim 1 wherein the control unit is further adapted to record data, in readable format, during the filling and venting process and wherein the method further comprises the step of causing the control unit to record data, in readable format, during the filling and venting process.

3. A method according to claim 2 wherein control unit records response of the air bubble detector.

4. A method according to claim 2 wherein the system includes controllable clamps or valves and wherein the control unit records indexing positions of controllable clamps or valves.

5. A method according to claim 2 wherein the system includes sensors for sensing filling levels of the reservoir and wherein the control unit records filling levels of the reservoir.

6. A method according to claim 2 wherein the system includes switches and wherein the control unit records switch-on and switch-off times.

7. A method according to claim 2 wherein the system includes pressure and flow sensors and wherein, during the filling and venting procedure, the control unit records pressure and flow data in readable form.

8. A method according to claim 1 wherein the method is carried out before the blood flow circuit is connected to the patient's vasculature.

9. A method according to claim 1 wherein the reservoir has upper and lower filling level sensors and a first controllable valve which controls venting of air from the circuit, wherein the control unit causes the first controllable valve to open when the lower filling level sensor senses liquid, thereby venting air from the circuit as the circuit filling with the filling fluid.

10. A method according to claim 9 wherein the control unit causes the first controllable valve to close when the upper filling level sensor of the reservoir senses liquid.

11. A method according to claim 1, wherein the method is carried out without tilting of any portion of the system.

12. A method according to claim 1 wherein the reservoir has an upper level sensor and a lower level sensor and the filter is positioned higher than the upper filling level sensor, and wherein the filling and venting process further causes the blood pump to run in a manner that causes the filter to become wetted with the filling fluid in incremental steps.

13. A method according to claim 1 wherein the bubble detector is located on the arterial blood outflow conduit, a quick action clamp is positioned on the arterial blood outflow conduit downstream of the bubble detector, a recirculation conduit extends between a location on the venous blood inflow conduit upstream of the reservoir and a location on the arterial blood outflow conduit between the bubble detector and the quick action arterial clamp; and wherein the control unit is programmed such that, if the bubble detector detects air bubbles in the priming fluid, the control unit maintains the quick action arterial clamp in a closed position and the priming fluid is recirculated from the arterial blood outflow conduit, through the recirculation conduit, back into the venous blood inflow conduit, through the reservoir, back into the arterial blood outflow conduit and again through the bubble detector until air bubbles are no longer detected in the priming fluid.

14. A system according to claim 13 wherein a bypass clamp is positioned on the recirculation conduit and wherein the control unit causes the bypass clamp to be open while the quick action clamp is closed, thereby allowing said recirculation of the priming fluid until air bubbles are no longer detected in the priming fluid.

* * * * *